United States Patent
Conner et al.

(10) Patent No.: US 10,828,004 B2
(45) Date of Patent: Nov. 10, 2020

(54) AUTOMATED QUANTITATIVE IMAGING SYSTEM

(71) Applicant: KONINKLIJKE PHILIPS N.V., Eindhoven (NL)

(72) Inventors: Joseph Conner, Shaker Heights, OH (US); Charles Nortmann, Richmond Heights, OH (US); Lingxiong Shao, Saratoga, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 182 days.

(21) Appl. No.: 15/520,874

(22) PCT Filed: Oct. 15, 2015

(86) PCT No.: PCT/IB2015/057905
§ 371 (c)(1),
(2) Date: Apr. 21, 2017

(87) PCT Pub. No.: WO2016/067145
PCT Pub. Date: May 6, 2016

(65) Prior Publication Data
US 2018/0021005 A1    Jan. 25, 2018

Related U.S. Application Data

(60) Provisional application No. 62/068,970, filed on Oct. 27, 2014.

(51) Int. Cl.
*A61B 6/00* (2006.01)
*A61B 6/03* (2006.01)
(Continued)

(52) U.S. Cl.
CPC ............. *A61B 6/545* (2013.01); *A61B 6/00* (2013.01); *A61B 6/03* (2013.01); *A61B 6/037* (2013.01);
(Continued)

(58) Field of Classification Search
CPC .. A61B 6/00; A61B 6/03; A61B 6/037; A61B 6/486; A61B 6/5205; A61B 6/545;
(Continued)

(56) References Cited

U.S. PATENT DOCUMENTS 6,510,336 B1 * 1/2003 Daghighian ............ G01T 1/161
250/370.06
10,215,864 B2 * 2/2019 Herraiz ................. G01T 1/1647
(Continued)

FOREIGN PATENT DOCUMENTS

FR        2867084       9/2005
WO     2006129301      12/2006
(Continued)

OTHER PUBLICATIONS

McCarthy, Timothy, et al. "The State of Positron Emitting Radionuclide Production in 1997." Jul. 1998. Seminars in Nuclear Medicine. vol. 28 Issue 3. pp. 235-246. (Year: 1998).*

*Primary Examiner* — Ahmed M Farah

(57) ABSTRACT

A quantitative imaging system (100) for automating delivery of a radiopharmaceutical and imaging a patient. The system (100) includes a QI controller (102) that controls the operation of the system. The system (100) includes a producer (104) for creating a radiopharmaceutical and a synthesizer (106) to synthesize the radioisotope with a biologically compatible material to form the radiopharmaceutical. The system (100) includes a dosimeter (110) to measure and timestamp the concentration measurement of the radiopharmaceutical and an injector (112) to deliver the radiophar-
(Continued)

maceutical into the patient. The system (100) includes an imaging apparatus (114) to image the patient. The QI controller (102) uses the timestamp of the concentration and decay characteristics to adjust imaging data. The system includes aquantitative analyzer (116) to calculate parametric images and quantitative values from the collected data.

20 Claims, 3 Drawing Sheets

(51) Int. Cl.
*A61M 5/00* (2006.01)
*A61M 5/172* (2006.01)
*A61M 5/50* (2006.01)
*G06T 11/00* (2006.01)

(52) U.S. Cl.
CPC ............ *A61B 6/486* (2013.01); *A61B 6/5205* (2013.01); *A61B 6/582* (2013.01); *A61M 5/007* (2013.01); *A61M 5/172* (2013.01); *A61M 5/5086* (2013.01); *G06T 11/003* (2013.01)

(58) Field of Classification Search
CPC ........... A61B 6/582; A61B 6/032; A61B 6/06; A61B 6/48; A61B 6/483; A61B 6/52; A61B 6/5211; A61B 6/5217; A61B 6/54; A61B 6/541; A61M 5/007; A61M 5/172; A61M 5/5086; A61M 5/168; A61M 5/16877; A61M 5/1723; A61M 5/1726; G06T 11/003
USPC .................... 600/431, 407, 425, 427, 436
See application file for complete search history.

(56) References Cited

U.S. PATENT DOCUMENTS

| | | |
|---|---|---|
| 2007/0073139 A1 | 3/2007 | Maschke |
| 2008/0233018 A1* | 9/2008 | van Dam ............ B01J 19/0093 422/159 |
| 2011/0137160 A1 | 6/2011 | Fago |
| 2011/0178359 A1* | 7/2011 | Hirschman ............ G16H 20/17 600/4 |
| 2013/0102772 A1 | 4/2013 | Eshima |
| 2015/0025371 A1* | 1/2015 | Georgi ................ A61B 6/4417 600/427 |

FOREIGN PATENT DOCUMENTS

| | | |
|---|---|---|
| WO | 2012064312 | 5/2012 |
| WO | 2013012798 | 1/2013 |
| WO | 2014087311 | 6/2014 |

* cited by examiner

PET

| Element | Radioisotope | Half-life | Production |
|---|---|---|---|
| Carbon | C-11 | 20.4 min | Cyclotron |
| Nitrogen | N-13 | 9.97 min | Cyclotron |
| Oxygen | O-15 | 122 sec | Cyclotron |
| Fluorine | F-18 | 110 min | Cyclotron |
| Gallium | Ga-68 | 67 min | Generator |
| Rubidium | Rb-82 | 75 sec | Generator |

SPECT

| Element | Radioisotope | Half-life | Production |
|---|---|---|---|
| Krypton | Kr-81m | 13 sec | Generator |
| Technetium | Tc-99m | 6.02 hrs | Generator |
| Iridium | Ir-191m | 5 sec | Generator |
| Gold | Au-195m | 30.5 sec | Generator |
| Tantalum | Ta-178 | 9.3 min | Generator |

FIG. 2

AUTOMATED QUANTITATIVE IMAGING SYSTEM

CROSS REFERENCE TO RELATED APPLICATIONS

This application is the U.S. National Phase application under 35 U.S.C. § 371 of International Application No. PCT/IB2015/057905, filed Oct. 15, 2015, published as WO 2016/067145 on May 6, 2016, which claims the benefit of U.S. Provisional Patent Application No. 62/068,970 filed Oct. 27, 2014. These applications are hereby incorporated by reference herein.

FIELD

The present application relates generally to medical imaging. It finds particular application in radioisotope based medical imaging, and will be described with particular reference thereto. However, it is to be understood that it also finds application in other usage scenarios and is not necessarily limited to the aforementioned application.

BACKGROUND

Medical imaging is an integral part of healthcare. The additional information provided by quantitative imaging aids in the evaluation of patients. Positron Emission Tomography (PET), Single Photon Emission Computed Tomography (SPECT), Magnetic Resonance Imaging (MRI), X-Ray Computed Tomography (CT), and Ultrasound all incorporate some form of quantitative imaging. Historically, PET has been recognized as the best for evaluation of metabolic parameters in vivo.

Metabolism and function are measured in PET through modelling of biologic processes. The models used apply to multiple radiopharmaceuticals. The radiopharmaceuticals are synthesized specifically for use in evaluating biologic processes. Positron emitting radionuclides used in PET are typically produced in cyclotrons. Close proximity of the production and imaging locations facilitates short half-life of the cyclotron produced nuclides. In order to perform the PET imaging and produce accurate quantitative results, the isotope production, delivery, and imaging are closely coordinated.

Historically, the process of generating quantitative images has been labor intensive. Most biological processes can be imaged better with very short half-time nuclides. The use of very short half-life nuclides, i.e. 20 minutes or less, involves a great deal of logistical coordination. Precursor materials and cyclotron operation are coordinated within a specific short time. Materials are provided at the appropriate time to the image suite. The patient must be positioned and prepared. Availability of the imaging system, for example, with very high count-rate performance, is coordinated with the radiopharmaceutical generation and delivery. The imaging system faithfully images a distribution of the radiopharmaceutical and/or a change in the distribution over time. The calculation of the metabolic parameters from the image data is a labor intensive process typically performed by highly-trained scientists.

SUMMARY

In accordance with one aspect, a quantitative imaging system comprises a delivery mechanism configured to create and deliver a radiopharmaceutical to a subject. The system further comprises an imaging apparatus configured to image the subject; and a quantitative controller communicatively linked to the delivery mechanism and imaging apparatus.

In accordance with another aspect, a method for quantitative imaging of a patient, comprises creating and delivering a radiopharmaceutical to a patient; receiving imaging data of a patient; and controlling the delivery of the radiopharmaceutical and imaging of the patient.

In accordance with another aspect, a quantitative imaging system, comprises a delivery mechanism configured to create and deliver a radiopharmaceutical to a patient to be imaged by an imaging apparatus; and a quantitative controller configured to control the delivery mechanism to create and deliver the radiopharmaceutical without human intervention. The delivery mechanism comprises a dose calibrator configured to sample the radiopharmaceutical for a concentration measurement of radioactive isotopes in the radiopharmaceutical and timestamps the measurement; a producer configured to convert a precursor material input into radioisotope; a synthesizer configured to synthesize the radioisotope with a biologically compatible material to form the radiopharmaceutical; and an injector configured to inject the radiopharmaceutical into the subject, wherein the producer, the synthesizer, the injector and the delivery mechanism are interconnected to convey the radioisotope to the synthesizer and the radiopharmaceutical between the synthesizer, the dosimeter and the delivery mechanism automatically without human intervention. The imaging apparatus system then takes an image or multiple images with respect to time. The system also includes an analyzer to calculate parametric images and quantitative values from the collected data.

One advantage resides in accurate coordination of generated image data with radiopharmaceutical remaining inside a patient, by accurately accounting for radioactive decay.

Another advantage resides in more accurate quantitative diagnostic information.

Another advantage resides in an automated process that streamlines delivery of a radiopharmaceutical to a patient.

Another advantage resides in less waste of initial starting material.

Still further advantages of the present invention will be appreciated to those of ordinary skill in the art upon reading and understanding the following detailed description.

BRIEF DESCRIPTION OF THE DRAWINGS

The present application may take form in various components and arrangements of components, and in various steps and arrangements of steps. The drawings are only for purposes of illustrating the preferred embodiments and are not to be construed as limiting the invention.

FIG. 2 lists radiopharmaceuticals and half-lives.

DETAILED DESCRIPTION OF EMBODIMENTS

The present application provides a system and method to automate quantitative metabolic imaging. The application provides for low-energy cyclotrons that are built for the production of specific radionuclides. The low-energy cyclotrons require few resources for siting and operation, and may be operated by an imaging technician. The present application provides for automatically compounding radiopharmaceuticals. Automated quality control may be performed. Delivery to an imaging apparatus may be automated. A digital PET system responds to the demands of imaging at a wide count range to faithfully represent the radiopharmaceutical distribution. Analysis may be performed using predefined models, and automated for the creation of metabolic values. The present application provides logistic control by a system that integrates monitoring of each of the components of the operation. This obviates or reduces the need for communication meetings between the personnel involved in the process. It is appreciated that the present disclosure is described using an exemplary digital PET system, however, other systems are contemplated.

Figure 1:
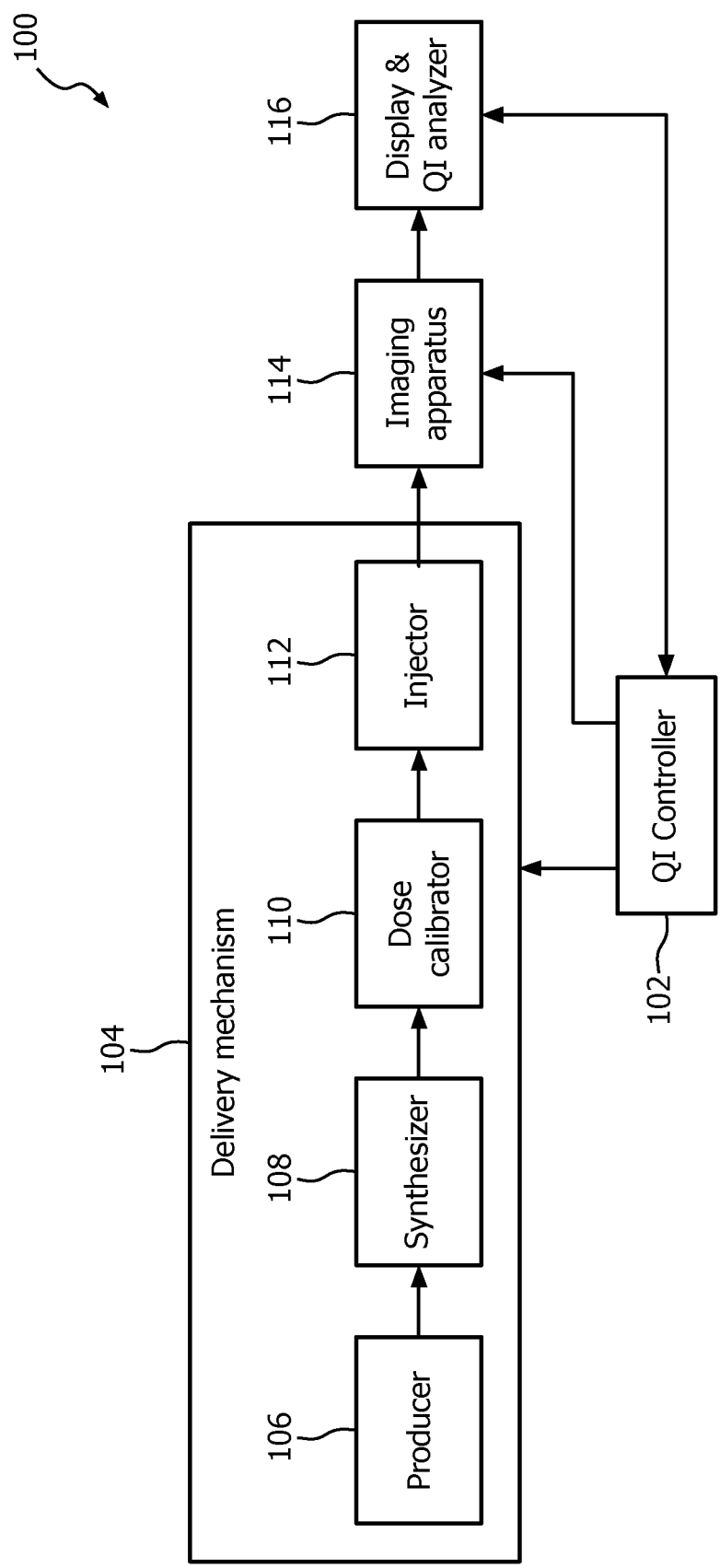
FIG. 1 depicts a quantitative imaging system.

With reference to FIG. 1, an automated quantitative imaging system 100 is depicted. A quantitative imaging (QI) controller 102 is interconnected to machines that perform different tasks for quantitative imaging. The QI controller 102 can be one or more processors, workstation or computer having a user input, display, keyboard, mouse and the like. The QI controller 102 controls and monitors the other hardware parts of the system in one place and automates quantitative imaging.

The QI controller 102 controls a delivery mechanism 104 that delivers a dose contrast radiopharmaceutical to a patient for imaging. The delivery mechanism 104 includes a radiopharmaceutical producer 106. The producer 106 creates a radioisotope from a precursor material. In one embodiment, the producer 106 is a cyclotron that uses proton bombardment to create radioisotopes. In another embodiment, the producer 106 is a generator. Radiopharmaceuticals used in imaging can have short half-lives which require injecting the patient soon after the radiopharmaceutical is generated. A half-life less than twenty minutes is considered a short half-life. For example, oxygen O-15 has a 122 second half-life which after 6 to 10 half-lives the radiopharmaceutical becomes ineffective for imaging purposes. A detailed example of the process for imaging a patient using oxygen O-15 radiopharmaceutical is described below.

With reference to FIG. 2, a table of radioisotopes and the corresponding half-lives is depicted for PET and SPECT imaging. Also shown is the type of production used to create each radioisotope, i.e. generator or cyclotron.

The producer 106 typically gives off radiation when creating the radiopharmaceutical from the precursor. Usually the producer 106 is located far away from the patient and an imaging system; however this is problematic for the short half-life radiopharmaceuticals. In the present application, the producer 106 is located near the patient and imaging system such that it is mechanically attached to the rest of the system, but also located such that the radiation from the producer 106 does not affect the rest of the system and patient. For example, the producer 106 can be located in a separate shielded room and then mechanically attached to the system through piping that can take the radiopharmaceutical to another room for further processing. This also provides utility for the delivery mechanism 104 to provide a constant flow of radiopharmaceutical as well batches. In another embodiment, the producer 106 is located in a centralized location and is mechanically/fluidly attached to more than one system for dosing a patient. This allows one producer 106 to provide radiopharmaceuticals to many imaging rooms, which is cost effective for hospital systems. In another embodiment, the producer 106 is a modular unit that is portable and mechanically attached to different systems as it is needed.

The producer 106 also includes a communications interface for communicating with one or more devices. Such communication may include sending information such as batch start time, radioisotope output time, substance(s), amount of precursor available, and etc. to the QI controller 102.

The delivery mechanism 104 includes a synthesizer 108. For some radioisotopes, the producer 106 outputs the radioisotope as a gas. The output of the producer 106 is mechanically attached, e.g. piped, to the input of the synthesizer 108. In one embodiment, a pump drives the flow of the radioisotope. The producer 106 and the synthesizer 108 are physically located relatively close to each other such that they can be mechanically attached. In one embodiment, the producer and synthesizer 108 are mechanically attached using a pipe. The synthesizer 108 formulates radiopharmaceutical by combining the radioisotope with a pharmaceutical agent. For example, O-15 gas is suspended in a biologically compatible liquid such as water, $H_2O$, to ease delivery to the patient. In one embodiment, the radiopharmaceutical can fill a reservoir until the patient is ready to be injected. In another embodiment, the QI controller 102 controls production and synthesis such that the radiopharmaceutical is delivered to the patient in a constant flow, thereby ensuring the least loss of radiation due to a short half-life. The synthesizer 108 also includes a communications interface for communicating with one or more devices.

The delivery mechanism 104 also includes a dose calibrator 110. The synthesizer 108 is mechanically attached in fluid communication to the dose calibrator 110. The dose calibrator 110 measures the concentration of the radioisotope and the time of the measurement. The dose calibrator 110 calculates the concentration in real time and sends the information back to the QI controller 102. From the concentration measurement, the time of the measurement, and the known decay rate of the isotope, the concentration of radioisotope for subsequent times is readily calculated. It is appreciated that the dose calibrator 110 can be disposed in the system at any location in the delivery mechanism 104 after synthesis and before injecting the patient. The dose measurement 110 also includes a communications interface for communicating with one or more devices. Such communication may include sending information such as the concentration and a timestamp identifying the time of the measurement. Knowing the timestamp aids in modeling the metabolic function of the patient because the QI controller 102 can better calculate the radioactive decay of the delivered radiopharmaceutical. It is appreciated that timestamps can be sent to the QI controller 102 at any part of the system from creation of the radiopharmaceutical to just before injection.

The delivery mechanism 104 also includes an injector 112, such as a syringe or pump for liquids, an inhalation system for gases, and the like. The dose calibrator 110 is connected, e.g. a pipe, to the injector 112 that physically delivers the radiopharmaceutical into the patient to be imaged. The dose calibrator 110 can be operatively coupled with the injector 112 to perform real time measurements while injecting the patient. The injector 112 is configured to administer one or more radiopharmaceuticals to the object or subject for a scan. The injector 112 is a single or multi-head injector with one or more bays configured to receive a radiopharmaceutical from a reservoir or pool. The injector 112 can inject the radiopharmaceutical in a selected volume and/or at a selected rate. When collecting the radiopharmaceutical in a reservoir, the QI controller 102 monitors the time since the concentration measure to just before injecting the patient. The QI controller 102 makes a determination based on the timestamp and measured concentration on whether the radiopharmaceutical can be used for imaging. If the radiopharmaceutical can still be used, the QI controller 102 controls the injector 112 to inject the patient. If the radiopharmaceutical cannot be used, the QI controller 102 discards the pooled radiopharmaceutical from the injector and controls the producer 106 to create more radiopharmaceutical after determining there is sufficient precursor to make the required amount of radiopharmaceutical.

The injector 112 also includes a user interface for programming the injector (e.g., delivery rate, delivery volume, delivery sequence, etc.), starting/stopping administration of the substance, etc., and a pressure sensor for determining delivery pressure. The injector 112 also includes a communications interface for communicating with one or more devices. Such communication may include sending information such as substance delivery start time, rate and/or volume, substance(s), pressure, stop time, and etc. to the QI controller 102.

The injector 112 is also communicatively linked with an imaging apparatus 114 through the QI controller 102. The imaging apparatus 114 is typically a PET, SPECT, or a hybrid system using a radiopharmaceutical for imaging. The hybrid system may include an MR, CT, ultrasound, projection x-ray, or other system that non-exclusively generates images of an interior of a subject.

The system clocks of the imaging apparatus 114, dose calibrator 110 and the injector 112 are synchronized with each other. The injector 112 and/or dose calibrator 110 can timestamp substance delivery information (e.g., rate, volume, pressure, etc.) and transmit the timestamped data to the QI controller 102. The QI controller 102 correlates the injection information with imaging information from the imaging apparatus 114 by correlating the time from the time stamps of the concentration measurement with the acquisition time of the projection and/or image data from the imaging apparatus 114. Of course, the injector 112 also sends other information to the QI controller 102 such as delivery start and stop time, information indicative of the point of delivery (e.g., arm, leg, etc.), and/or other information.

The QI controller 102 can control the injector 112 to inject the patient in synchronized timing with imaging the patient with the imaging apparatus 114, at selected intervals from time zero and the like. The imaging apparatus 114 sends imaging data to the QI controller 102 for reconstruction according to metabolic models that are dependent on the timestamp of the radiopharmaceutical. The QI controller 102 coordinates the information needed for a QI analyzer 116 to determine a standard uptake value (SUV), washout rates, kinetic models, and the like for each voxel with better accuracy through better knowledge of the radioactive decay, i.e. half-life calculations, of the radiopharmaceutical within the patient during imaging and before the radiopharmaceutical is injected into the patient. In one embodiment, instead of calculating decay based on timestamp, the QI controller 102 receives measurements of the actual decay from two different points in the system, which can be used to model the decay of the radiopharmaceutical inside the patient during imaging.

In an exemplary embodiment, oxygen O-15 is used to image a cardiology patient. Due to the short half-life of O-15, a constant flow of O-15 is desired to be delivered to the patient. The QI controller 102 controls the delivery mechanism 104 that delivers oxygen O-15 to the patient. The delivery mechanism 104 controls the producer 106, in this example a cyclotron, to begin creating the O-15 from the precursor material provided to the producer 106. The producer 106 creates the O-15 through a proton bombardment.

The delivery mechanism 104 controls the O-15 output in gas form from the producer 106 to the synthesizer 108. The O-15 is piped to the synthesizer 108. Typically, radiopharmaceuticals are formulated with a substance or fluid that is compatible with a human body, often a substance a human body uses such as water, sugar, iodine, and the like. In a perfusion embodiment, the synthesizer 108 converts the O-15 from a gas to a liquid by suspending the O-15 in water $H_2O$. The [O-15]$H_2O$ radiopharmaceutical leaves the synthesizer 108 and flows via piping through the dose calibrator 110 that samples and timestamps the radiopharmaceutical concentration as it flows via piping to the injector 112. The injector 112 injects the patient with the [O-15]$H_2O$ after it receives it from the dose calibrator 110. The prepared [O-15]$H_2O$ is delivered for each patient use, so excess is not prepared. The QI controller 102 controls the injection of the [O-15]$H_2O$ by the injector 112 in temporal coordination with imaging the patient with the imaging apparatus 114. The QI controller 102 automatically records activity to be administered. The O-15 passes through cell membranes and is metabolized by healthy cardiac and other tissue. Very little, if any, O-15 passes into necrotic tissue. Damaged tissue, e.g. damaged by a heart attack, uptakes the O-15 more slowly. The O-15 form [O-15]$CO_2$ which passes back to the blood to be exhaled by the lungs. A time sequence of images is generated which shows the uptake as washout versus time. After normalizing the images to compensate for the decay of the O-15 from the time between the concentrations measurement and each image based on the known decay curve for O-15. For example, the myocardium can be imaged from subtracting an initial image taken before perfusion from subsequent images. The image intensity between the images is adjusted for the O-15 decay. The series of images adjusted for O-15 decay can be compared, e.g. subtracted, to determine the health of various regions of the myocardium. The QI analyzer 116 performs serial studies for rest and stress. For reconstruction, the QI analyzer 116 incorporates automatic calculation of absolute flow in ml/min/g. with high accuracy. The QI analyzer 116 generates parametric maps of regional flow related to expected normal flow. The QI controller 102 facilitates calculation of coronary flow reserve with greater accuracy. After reconstruction, the reconstructed images are quantitatively analyzed and displayed on a display of the QI analyzer 116.

In another example, F-18 is generated by the producer 106. The synthesizer combines the F-18 with glucose to form F-18 flourodeoxyglucose (FDG). The FDG is injected and imaged, and the concentrations of F-18 in the images are corrected as above. The FDG is preferentially taken up by voracious tissues, such as cancer tumors. From the normalized FDG, image uptake and washout values can be calculated to locate cancer cells, monitor cancer progression, monitor cancer treatment progress, and the like.

Numerous other applications using the isotopes of FIG. 2 and the like, as are known in the art, are also contemplated.

Figure 3:
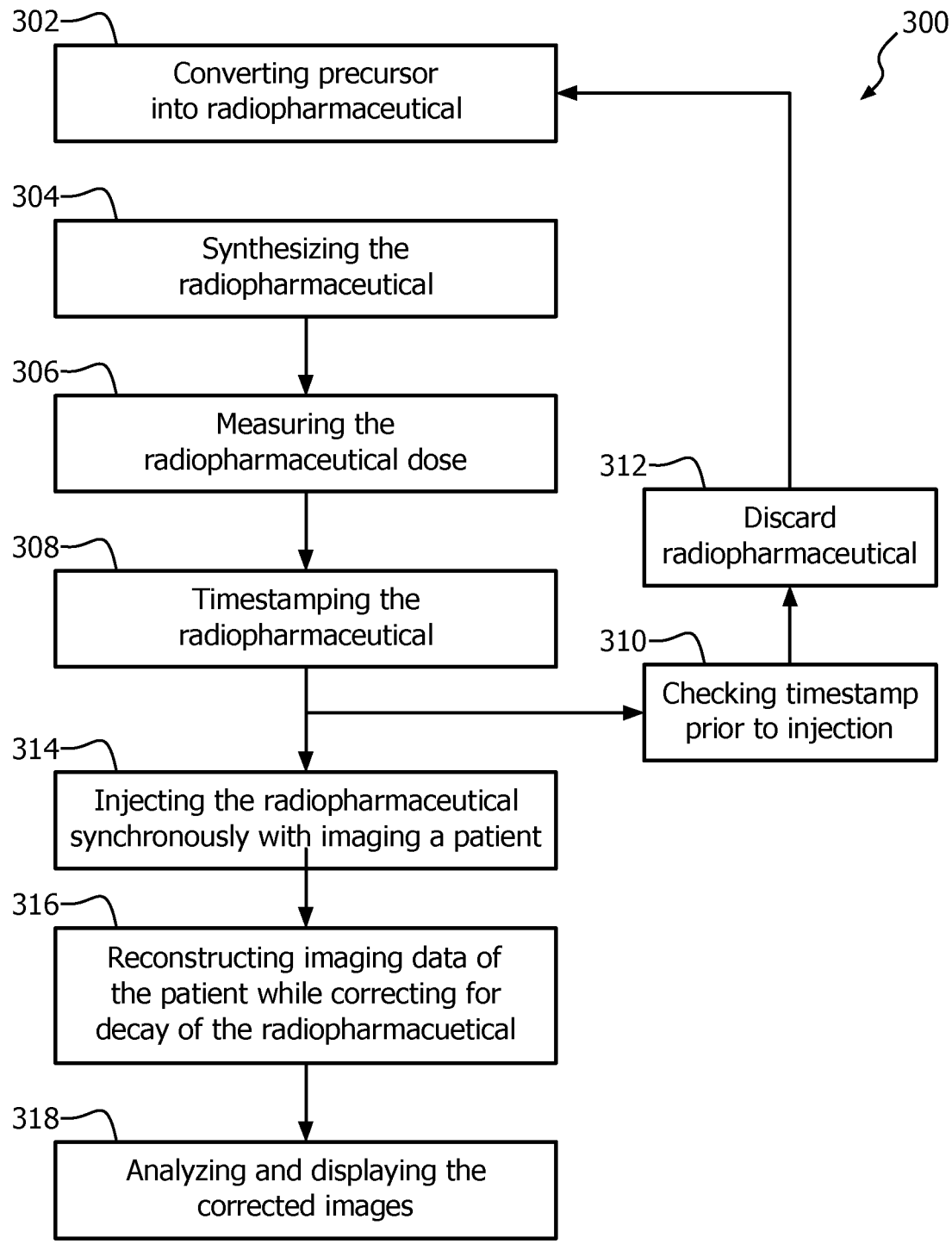
FIG. 3 depicts a method for quantitative imaging.

With reference to FIG. 3, a method for automated quantitative imaging 300 is depicted. At a step 302, a precursor material is converted into a radioisotope. At a step 304, the radioisotope is automatically delivered to a synthesizer 108 to be synthesized into a radiopharmaceutical that is deliverable to a patient. At a step 306, the synthesized radiopharmaceutical is measured for radioisotope concentration and continually at a step 308, the measurement is timestamped. The concentration and timestamp are sent to the QI controller 102. At a step 310, the timestamp is compared to the time just prior to injection of the patient. The QI controller 102 determines whether the radiopharmaceutical is still effective for imaging the patient due to radioactive decay. If the QI controller 102 determines too much decay has occurred based on the timestamp, at a step 312, the QI controller controls the injector 112 to discard the radiopharmaceutical and repeat the process at step 302. The QI controller can optionally check whether there is enough precursor available to convert into a radiopharmaceutical for step 302. If the QI controller 102 determines the radiopharmaceutical is effective, at a step 314, the radiopharmaceutical is injected into the patient and the patient is imaged with the imaging apparatus 114. At a step 316, the imaging data is reconstructed from imaging the patient. The imaging data is corrected for radioactive decay. At a step 318, the corrected and reconstructed images are quantitatively analyzed and displayed on using the QI analyzer and display 116. The quantitative analyzer 116 includes all kind of imaging parameters estimation methods, which relate to the biological behavior of targeted disease. A common term of such parameter estimation is called quantitative imaging.

As used herein, a memory includes any device or system storing data, such as a random access memory (RAM) or a read-only memory (ROM). Further, as used herein, a processor includes any device or system processing input device to produce output data, such as a microprocessor, a microcontroller, a graphic processing unit (GPU), an application-specific integrated circuit (ASIC), a FPGA, and the like; a controller includes any device or system controlling another device or system, and typically includes at least one processor; a user input device includes any device, such as a mouse or keyboard, allowing a technician of the user input device to provide input to another device or system; and a display device includes any device for displaying data, such as a liquid crystal display (LCD) or a light emitting diode (LED) display.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A quantitative imaging system, comprising:
   a delivery mechanism configured to create and deliver a radiopharmaceutical to a subject, the delivery mechanism including:
   a cyclotron configured to convert a precursor material input into radioisotope,
   a synthesizer configured to synthesize the radioisotope with a biologically compatible material to form the radiopharmaceutical, and
   an injector configured to inject the radiopharmaceutical into the subject,
   wherein the cyclotron, the synthesizer, and the injector are interconnected to convey the radioisotope from the cyclotron to the synthesizer, and to convey the radiopharmaceutical from the synthesizer to the injector automatically, all without human intervention;
   an imaging apparatus configured to image the subject; and
   a quantitative imaging controller communicatively linked to the delivery mechanism and imaging apparatus,
   wherein the quantitative imaging controller is configured to control the cyclotron and the synthesizer such that the radiopharmaceutical is delivered to the subject in a constant flow.

2. The quantitative imaging system according to claim 1, wherein the delivery mechanism further includes:
   a dose calibrator configured to sample the radiopharmaceutical for concentration measurements of radioactive isotopes in the radiopharmaceutical, and to timestamp the concentration measurements.

3. The quantitative imaging system according to claim 2, wherein the quantitative imaging controller is configured to adjust imaging data generated by the imaging apparatus based on a time the dose calibrator measures the concentration of the radioisotope and radiation decay characteristics of the radioisotope to produce adjusted imaging data.

4. The quantitative imaging system according to claim 3, wherein the quantitative imaging controller reconstructs the adjusted imaging data into images of the patient.

5. The quantitative imaging system according to claim 2, wherein the quantitative imaging controller uses the timestamp for controlling the delivery of the radiopharmaceutical to the patient.

6. The quantitative imaging system according to claim 2, wherein the imaging apparatus is configured to generate a temporal series of timestamped images and the imaging system and/or the quantitative imaging controller are configured to adjust the timestamped images based on the timestamps of the concentration measurements and the timestamped images, and radiation decay characteristics of the radioisotope.

7. The quantitative imaging system of claim 1, wherein the radioisotope comprises O-15.

8. The quantitative imaging system of claim 1, wherein the imaging apparatus is configured to perform positron emission tomography (PET) imaging.

9. A method for quantitative imaging a patient, the method comprising:
   creating a radiopharmaceutical for a patient by using proton bombardment in a cyclotron to convert a precursor material into a radioisotope, and synthesizing the radioisotope with a biologically compatible material to form a radiopharmaceutical;
   delivering the radiopharmaceutical to the patient by injecting the radiopharmaceutical into the patient, wherein the cyclotron performing the converting, and devices performing the synthesizing and the injecting, are interconnected to convey the radioisotope for synthesis, and the radiopharmaceutical between synthesis and delivery, automatically without human intervention;
   receiving imaging data of a patient; and
   controlling the creation of the radiopharmaceutical and the delivery of the radiopharmaceutical to the patient during the receiving of the imaging data of the patient such that the radiopharmaceutical is delivered to the patient in a constant flow.

10. The method according to claim 9, wherein delivering the radiopharmaceutical includes:
   sampling the radiopharmaceutical for a concentration measurement of radioactive isotopes in the radiopharmaceutical; and
   timestamping the concentration measurement.

11. The method according to claim 10, including:
   generating imaging data of the subject; and
   adjusting the imaging data based on time since the concentration measurement of the radioisotope and radiation decay characteristics of the radioisotope.

12. The method according to claim 10, including:
   controlling the delivery to the patient using the timestamp.

13. The method according to claim 10, including:
generating a temporal series of timestamped images; and
adjusting the images based on the timestamps of the concentration measurement and the images and radiation decay characteristics of the radioisotope.

14. The method according to claim 13, including:
reconstructing the adjusted imaging data into diagnostic images of the patient.

15. The method according to claim 9, wherein the radioisotope comprises 0-15.

16. The method of claim 9, wherein the imaging data comprises positron emission tomography (PET) imaging data.

17. A radiopharmaceutical delivery system, comprising:
a delivery mechanism configured to create a radiopharmaceutical and to deliver the radiopharmaceutical to a patient to be imaged by an imaging apparatus, wherein the delivery mechanism includes:
   a dose calibrator configured to sample the radiopharmaceutical for a concentration measurement of radioactive isotopes in the radiopharmaceutical, and to timestamp the concentration measurement;
   a cyclotron configured to convert an input precursor material into a radioisotope,
   a synthesizer mechanically attached to the cyclotron and to the dose calibrator, and configured to synthesize the radioisotope with a biologically compatible material to form the radiopharmaceutical, and
   an injector configured to inject the radiopharmaceutical into the subject,
   wherein the cyclotron, the synthesizer, and the injector are interconnected to convey the radioisotope from the cyclotron to the synthesizer, and to convey the radiopharmaceutical between the synthesizer, the dose calibrator and the injector automatically, all without human intervention; and
a quantitative imaging controller configured to control the cyclotron and the synthesizer to create and deliver the radiopharmaceutical to the patient without human intervention.

18. The radiopharmaceutical delivery system of claim 17, wherein the quantitative imaging controller uses the timestamp for controlling the delivery of the radiopharmaceutical to the patient.

19. The radiopharmaceutical delivery system of claim 17, wherein the radioisotope comprises O-15.

20. The radiopharmaceutical delivery system of claim 17, wherein the synthesizer is mechanically attached to the cyclotron via a pipe.

* * * * *